United States Patent
Peng et al.

(10) Patent No.: US 7,294,729 B2
(45) Date of Patent: Nov. 13, 2007

(54) BIS-CHELATING LIGAND AND USE THEREOF IN CARBONYLATION PROCESSES

(75) Inventors: Wei-Jun Peng, Hurricane, WV (US); Johnathan E Holladay, Kennewick, WA (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 469 days.

(21) Appl. No.: 10/527,568

(22) PCT Filed: Sep. 26, 2003

(86) PCT No.: PCT/US03/30380

§ 371 (c)(1),
(2), (4) Date: Mar. 11, 2005

(87) PCT Pub. No.: WO2004/035595

PCT Pub. Date: Apr. 29, 2004

(65) Prior Publication Data

US 2006/0058557 A1    Mar. 16, 2006

Related U.S. Application Data

(60) Provisional application No. 60/418,620, filed on Oct. 15, 2002.

(51) Int. Cl.
    *C07F 15/00*    (2006.01)
    *C07F 9/02*     (2006.01)
    *B01J 31/00*    (2006.01)

(52) U.S. Cl. .......................... 556/12; 556/18; 556/404; 558/77; 558/78; 568/12; 568/14; 568/451; 502/158; 502/162

(58) Field of Classification Search .................. 556/12, 556/18, 404; 568/12, 14, 451; 558/77, 78; 502/158, 162
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,247,486 A | 1/1981 | Brewester et al. |
| 4,599,206 A | 7/1986 | Billig et al. |
| 4,748,261 A | 5/1988 | Billig et al. |

(Continued)

FOREIGN PATENT DOCUMENTS

DE    19602301 A1    7/1996

(Continued)

OTHER PUBLICATIONS

Chemical Abstracts No. 125:33742.

(Continued)

*Primary Examiner*—Porfirio Nazario-Gonzalez
(74) *Attorney, Agent, or Firm*—Marie F. Zuckerman

(57) ABSTRACT

A novel bis-chelating composition characterized by formula I: wherein M is a Group VB element; R1 and R2 are each independently selected from hydrogen and monovalent hydrocarbyl radicals; or R1 and R2 are bonded together to form a diradical; or one of R1 or R2 is hydrogen or a monovalent hydrocarbyl radical, while the other of R1 or R2 is a hydrocarbyl radical bonded to an atom in Ar; wherein Ar is selected from 1,2-arylenes; Q is selected from 1,2-arylenes, 2,2'-bisarylenes and alkyl diradicals; and W is selected from II, III, IV, or V: wherein M is as defined hereinbefore; each R is independently selected from hydrogen and monovalent hydrocarbyl radicals; X is selected from alkyl and aryl diradicals; $Ar^1$ and $Ar^2$ are each independently selected from 1,2-arylenes; $Ar^3$ and $Ar^4$ are each independently selected from monovalent aryl radicals; and n in formula IV is 0 or 1. The composition finds utility as a ligand in catalysts for carbonylation processes

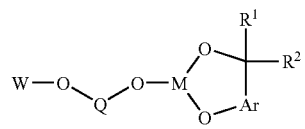

(I)

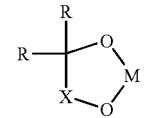

(II)

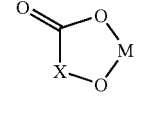

(III)

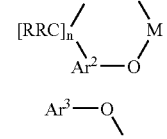

(IV)

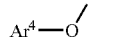

(V)

35 Claims, No Drawings

U.S. PATENT DOCUMENTS

| | | | |
|---|---|---|---|
| 4,755,625 A | | 7/1988 | Maerkl et al. |
| 4,947,003 A | * | 8/1990 | Davis et al. .................. 568/454 |
| 5,105,018 A | * | 4/1992 | Miyazawa et al. ........... 568/453 |
| 5,874,641 A | | 2/1999 | Burke et al. |
| 5,929,289 A | | 7/1999 | Abatjoglou et al. |
| 5,962,744 A | * | 10/1999 | Ojima et al. ................. 568/454 |
| 6,156,936 A | | 12/2000 | Drent et al. |
| 6,570,033 B2 | * | 5/2003 | Rottger et al. ................ 558/78 |
| 7,196,230 B2 | * | 3/2007 | Peng et al. .................. 568/451 |

FOREIGN PATENT DOCUMENTS

| | | |
|---|---|---|
| EP | A1-213639 A2 | 3/1987 |
| EP | A1-353770 A2 | 2/1990 |
| EP | A1-569328 A1 | 11/1993 |
| EP | A1-1008581 A1 | 6/2000 |
| EP | A1-1099677 A1 | 5/2001 |
| EP | A1-1099678 A1 | 5/2001 |
| EP | A1-1201675 A1 | 5/2002 |
| JP | 9-87292 | 3/1997 |
| WO | WO 95/14659 A1 | 6/1995 |
| WO | WO 00/09467 A1 | 2/2000 |
| WO | WO 01/58589 A1 | 8/2001 |
| WO | WO 01/85739 A1 | 11/2001 |
| WO | WO 02/00670 A1 | 1/2002 |
| WO | WO 03/016320 A1 | 2/2003 |
| WO | WO 03/078444 A2 | 9/2003 |

OTHER PUBLICATIONS

Chemical Abstracts No. 124:56087.

Chemical Abstracts No. 118:102081.

C. Botteghi et al., Journal of Molecular Catalysis, A, Chemical, 1999, 143, pp. 311-323.

D. Selent, et al., Angewandte Chemie, Intl. Edition, 2001, 40 (9), pp. 1696-1698.

S. D. Pastor et al., Inorganic Chemistry, 1996, 35 (4), 949-958.

Peng, Wei-Jun, "Bisphosphite Ligands for Carbonylation Process", Co-pending U.S. Appl. No. 10/504,247, filed Mar. 4, 2003: (equivalent to WO 2003/078444 above).

* cited by examiner

BIS-CHELATING LIGAND AND USE THEREOF IN CARBONYLATION PROCESSES

CROSS REFERENCE TO RELATED APPLICATION

This patent application claims the benefit of U.S. provisional application Ser. No. 60/418,620, filed on Oct. 15, 2002.

BACKGROUND OF THE INVENTION

This invention relates to a bis-chelating ligand composition, particularly of Group VB elements (P, As, Sb), and its use in transition metal complex catalyzed reactions. Preferably, this invention relates to a bis-chelating ligand composition, particularly of Group VB elements, and its use in transition metal-ligand complex catalyzed carbonylation processes, preferably, hydroformylation processes.

Carbonylation processes directed to the production of oxygenated products are well known and generally involve reaction of an organic compound with carbon monoxide and often a third reactant, preferably, hydrogen. See, for example, J. Falbe, "New Syntheses With Carbon Monoxide," Springer Verlag, New York, 1980. Such processes may include the carbonylation of organic compounds, such as olefins, acetylenes, alcohols, and activated chlorides, with carbon monoxide, and optionally, either hydrogen, alcohol, amine, or water, as well as ring closure reactions of functionally unsaturated compounds, for example, unsaturated amides, with carbon monoxide. One major class of known carbonylation processes comprises the hydroformylation of an olefinic compound with carbon monoxide and hydrogen to produce aldehydes, followed if desired by reduction of the aldehyde to alcohol; or reductive amination of the aldehyde to amine; or oxidation of the aldehyde to carboxylic acid; or aldolization of the aldehyde followed by oxidation to hydroxyacid. Oxygenated products, such as alcohols, carboxylic acids, and hydroxyacids find utility in a multitude of applications, including as solvents, surfactants, monomers for the preparation of polymers, and as intermediates in the synthesis of pharmaceuticals and other industrial chemicals.

Carbonylation processes are known to be facilitated by metal-ligand complex catalysts, such as Group VIII transition metal-phosphorus ligand complex catalysts. Representative art disclosing a variety of hydroformylation catalysts of various triorganophosphine, triorganophosphite, diorganophosphite, and bisphosphite ligands is found in the following references: U.S. Pat. No. 3,527,809; U.S. Pat. No. 4,599,206; U.S. Pat. No. 4,748,261; and WO-A1-02/00670. Likewise, triorganoarsine and triorganoantimony ligands are known for analogous carbonylation processes as disclosed, for example, in WO-A1-01/085739, WO-A1-01/058589, WO-A1-00/009467, U.S. Pat. No. 6,156,936, and U.S. Pat. No. 4,755,625. Disadvantageously, many of the transition metal-ligand complex catalysts disclosed for these carbonylation processes exhibit undesirably low activity or insufficient stability. More disadvantageously, many of the disclosed transition metal-ligand complex catalysts exhibit high isomerization selectivity of long chain alpha-olefins to internal olefins. Even more disadvantageously, many of the ligands disclosed in the art cannot be easily fine-tuned to provide high selectivity to the desired hydroformylation product.

In view of the above, a search continues in the art to find novel bis-chelating ligands that will provide improved activity, improved stability, improved isomerization selectivity, and/or improved ease of fine-tuning selectivity in carbonylation processes, preferably, hydroformylation processes.

SUMMARY OF THE INVENTION

In a first aspect, this invention provides for a novel bis-chelating ligand composition represented by generic formula I below:

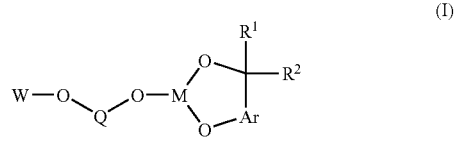

(I)

wherein M is a Group VB element selected from phosphorus (P), arsenic (As), or antimony (Sb); $R^1$ and $R^2$ are each independently selected from hydrogen and monovalent hydrocarbyl radicals; or $R^1$ and $R^2$ are bonded together to form a hydrocarbyl or substituted hydrocarbyl diradical that together with the methylene carbon of formula I forms a cyclic or heterocyclic ring; or alternatively, one of $R^1$ or $R^2$ is hydrogen or a monovalent hydrocarbyl radical, while the other of $R^1$ or $R^2$ is a hydrocarbyl or substituted hydrocarbyl radical bonded to an atom in the aryl group Ar to form a cyclic or heterocyclic ring. Further to formula I, Ar is selected from 1,2-arylenes; Q is selected from the group consisting of 1,2-arylenes, 2,2'-bisarylenes and allyl diradicals; and W is selected from the group consisting of Group VB element-containing formulas II, III, IV, and V:

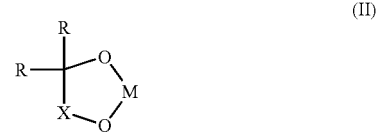

(II)

(III)

(IV)

(V)

wherein M is as defined hereinbefore; each R is independently selected from hydrogen and monovalent hydrocarbyl radicals; X is selected from alkyl and aryl diradicals; $Ar^1$ and $Ar^2$ are each independently selected from 1,2-arylenes; $Ar^3$ and $Ar^4$ are each independently selected from monovalent aryl radicals; and n in formula IV is 0 or 1. If n is 0, the aryl radicals $Ar^1$ and $Ar^2$ are directly connected by a single carbon-carbon bond from one ring to the other.

The novel bis-chelating ligand composition of this invention finds utility in catalyst and catalyst precursor compositions that are used in carbonylation processes, preferably, hydroformylation processes. As compared with prior art catalysts, the novel bis-chelating ligand composition of this invention advantageously provides for carbonylation catalysts of greater overall activity and stability, of greater selectivity to linear aldehydes, of reduced isomerization of terminal to internal olefins, and of improved ease of fine-tuning selectivity. By employing the novel bis-chelating ligand of this invention, for example, a yield of essentially 93 mole percent n-nonanals can be achieved in the hydroformylation of 1-octene.

In a second aspect, this invention provides for a novel complex catalyst or complex catalyst precursor composition comprising a Group VIII transition metal bonded to at least one molecule of ligand of formula I hereinabove, the transition metal optionally being further bonded to carbon monoxide, hydrogen, or both carbon monoxide and hydrogen.

In a third and related aspect, this invention provides for a novel complex catalyst solution or complex catalyst precursor solution comprising a solvent, a complex catalyst or catalyst precursor composition comprising a Group VIII transition metal bonded to at least one ligand, with the solution optionally further comprising free ligand; wherein the bonded and free ligands are represented by formula I hereinabove; and wherein optionally the Group VIII transition metal may be further bonded to carbon monoxide, hydrogen, or both carbon monoxide and hydrogen. The novel catalyst or catalyst precursor composition and the novel solution thereof find utility particularly in carbonylation processes, preferably, hydroformylation processes. Beneficially, the novel carbonylation catalyst of this invention provides for a more active and more selective carbonylation catalyst, as compared with prior art carbonylation catalysts.

In a fourth aspect, this invention provides for a novel carbonylation process comprising contacting an organic compound capable of being carbonylated with carbon monoxide in the presence of a Group VIII transition metal-ligand complex catalyst, wherein the ligand is represented by formula I hereinabove, the contacting being conducted under carbonylation conditions sufficient to prepare the corresponding carbonylated organic compound. The novel carbonylation process of this invention, including a preferred hydroformylation process of this invention, finds utility in the production of useful organic intermediates, solvents, and monomers. n-Nonanal and methyl 11-hydroxyundecanoate are examples of such useful organic monomers that can be prepared from n-octene and methyl 1-decenoate, respectively, using the carbonylation catalyst and hydroformylation process of this invention.

DETAILED DESCRIPTION OF THE INVENTION

In a primary aspect, the invention described herein pertains to a novel bis-chelating ligand composition, hereinafter referred to as the "ligand composition," which is represented by the following generic formula I:

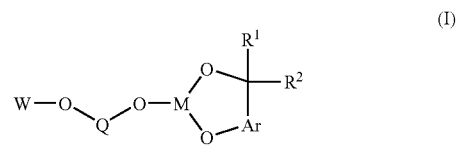

wherein M is a Group VB element selected from phosphorus (P), arsenic (As), or antimony (Sb); $R^1$ and $R^2$ are each independently selected from hydrogen and monovalent hydrocarbyl radicals; or $R^1$ and $R^2$ are bonded together to form a hydrocarbyl or substituted hydrocarbyl diradical that together with the illustrated methylene carbon (that is, carbon bonded to $R^1$, $R^2$, O, and Ar) forms a cyclic or heterocyclic ring (for example, with O, N, S hetero atom); or alternatively, one of $R^1$ or $R^2$ is hydrogen or a monovalent hydrocarbyl radical, while the other of $R^1$ or $R^2$ is a hydrocarbyl or substituted hydrocarbyl radical bonded to an atom in the aryl group Ar to form a cyclic or heterocyclic ring. Further to formula I, Ar is selected from 1,2-arylenes; Q is selected from the group consisting of 1,2-arylenes, 2,2'-bisarylenes and alkyl diradicals; and W is selected from the Group VB radical-containing formulas II, III, IV, and V:

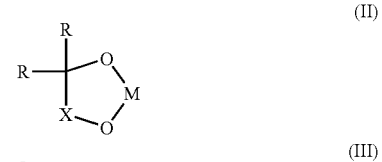

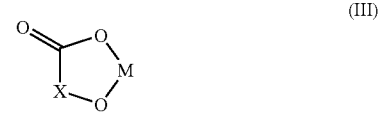

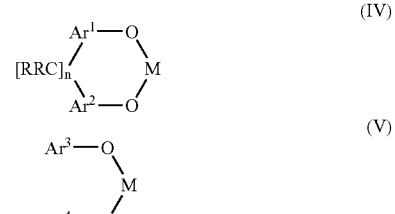

wherein M is independently selected as defined hereinbefore; each R is independently selected from hydrogen and monovalent hydrocarbyl radicals; X is selected from alkyl and aryl diradicals; $Ar^1$ and $Ar^2$ are each independently selected from 1,2-arylenes; and $Ar^3$ and $Ar^4$ are each independently selected from monovalent aryl radicals; and in formula IV, n is 0 or 1. If n is 0, $Ar^1$ and $Ar^2$ are bonded by a single carbon-carbon bond directly connecting $Ar^1$ to $Ar^2$.

Preferably, each M is phosphorus. Preferably, each $R^1$ and $R^2$ is independently selected from hydrogen, $C_{1-20}$ primary alkyl radicals, and substituted $C_{1-20}$ primary alkyl radicals; or preferably, $R^1$ and $R^2$ are bonded together to form a $C_{2-7}$ diradical that together with the illustrated methylene carbon forms a $C_{3-8}$ cyclic or heterocyclic ring (preferably, heteroatom N or O). In an alternative preferred embodiment, one of $R^1$ or $R^2$ is a $C_{1-20}$ primary alkyl radical, while the other of $R^1$ or $R^2$ is joined with an atom in the aryl group Ar to form a $C_{5-8}$ cyclic or heterocyclic ring (preferably, heteroatom N or O). Preferably, Ar is a $C_{6-20}$ 1,2-arylene or a substituted derivative thereof. Preferably, Q is selected from the group consisting of $C_{6-20}$ 1,2 arylenes, $C_{12-30}$ 2,2'-bisarylenes, $C_{1-20}$ alkyl diradicals, and substituted derivatives thereof. Preferably, each R is selected from hydrogen, $C_{1-20}$ primary alkyl radicals and substituted $C_{1-20}$ primary alkyl radicals. Preferably, X is selected from $C_{1-20}$ alkyl and $C_{6-20}$ aryl diradicals, and substituted derivatives thereof. Preferably, $Ar^1$ and $Ar^2$ are each independently selected from $C_{6-20}$ 1,2-arylenes and substituted derivatives thereof. Preferably, $Ar^3$ and $Ar^4$ are each independently selected from $C_{6-20}$ monovalent aryl radicals and substituted derivatives thereof. Suitable substituents for any of the aforementioned radicals include any substituent that is non-interfering with the use of the composition as a ligand in a metal complex catalyst; particular species of substituents being mentioned hereinafter.

Suitable examples of $R^1$ and $R^2$ in formula I include, without limitation, hydrogen, methyl ethyl n-propyl, n-butyl isobutyl, neo-pentyl, and the various normal and branched isomers of hexyl, heptyl, octyl, nonyl and decyl monovalent primary radicals. When $R^1$ and $R^2$ are bonded together to form a diradical, suitable examples of such include, without limitation, 1,4-butylene (—$CH_2CH_2CH_2CH_2$—), 1,5-pentylene (—$CH_2CH_2CH_2CH_2CH_2$—), and the like. Suitable examples of Ar in formula I include, without limitation, 1,2-phenylene, 1,2-naphthylene, and 2,3-naphthylene, and various substituted derivatives thereof, including 3-methyl-1,2-phenylene, 3-ethyl-1,2-phenylene, 3-isopropyl-1,2-phenylene, 3,5-dimethyl-1,2-phenylene, 3,5-diethyl-1,2-phenylene, 3,5-diisopropyl-1,2-phenylene, 3-methyl-1,2-naphthylene, and 1-methyl-2,3-naphthylene. Suitable examples of Q in formula I include, without limitation, 2,2'-biphenyl, 3,3'-di-tert-butyl-2,2'-biphenyl, 3,3'-bis(trimethylsilyl)-5,5'-di-tert-butyl-2,2'-biphenyl, 3,3',5,5'-tetra-tert-butyl-2,2'-biphenyl, 3,3'-di-tert-butyl-5,5'-dimethoxy-2,2'-biphenyl, 3,3',5,5'-tetra-tert-amyl-2,2'-biphenyl, 3,3'-diphenyl-5,5'-di-tert-butyl-2,2'-biphenyl, 3,3'-di-tert-butyl-5,5'-bis(trimethylsilyl)-2,2'-biphenyl, 3,3'-bis(trimethylsilyl)-5,5'-bis(2,4,6-trimethylphenyl)-2,2'-biphenyl, ethylene (—$CH_2CH_2$—), 1,3-propylene (—$CH_2CH_2CH_2$—), 1,2-phenylene (—$C_6H_4$—), 1,2-naphthylene (—$C_{10}H_6$—), 2,3-naphthylene (—$C_{10}H_6$—), 3,5-dichloro-1,2-phenylene, 3,5-dibromo-1,2-phenylene, 3-iodo-5-methyl-1,2-phenylene, 3,5-diisopropyl-1,2-phenylene, 3,5,6-trichloro-1,2-phenylene, 3-phenyl-1,2-phenylene, 1,1-diethyl-1,1-methylene, 1,1-cyclohexylidene, 1,1-cycloheptylidene, and 3-isopropyl-6-methyl-1,2-phenylene.

Suitable examples of R in formulas II and IV include, without limitation, methyl, ethyl, n-propyl, n-butyl, isobutyl, neo-pentyl, and the various normal and branched isomers of hexyl, heptyl, octyl, nonyl, and decyl monovalent primary radicals. Suitable examples of X in formulas II and m include, without limitation, methylene (—$CH_2$—), ethylene (—$CH_2CH_2$—), 1,3-propylene (—$CH_2CH_2CH_2$—), 1,2-phenylene (—$C_6H_4$—), 1,2-naphthylene (—$C_{10}H_6$—), 2,3-naphthylene (—$C_{10}H_6$—), 3,5-dichloro-1,2-phenylene, 3,5-dibromo-1,2-phenylene, 3-iodo-5-methyl-1,2-phenylene, 3,5-diisopropyl-1,2-phenylene, 3,5,6-trichloro-1,2-phenylene, 3-phenyl-1,2-phenylene, 1,1-diethyl-1,1-methylene, 1,1-cyclohexylidene, 1,1-cycloheptylidene, and 3-isopropyl-6-methyl-1,2-phenylene. Suitable examples of $Ar^1$ and $Ar^2$ in formula IV include, without limitation, 1,2-phenylene, methyl-1,2-phenylene, ethyl-1,2-phenylene, isopropyl-1,2-phenylene, 5-tert-butyl-1,2-phenylene, dimethyl-1,2-phenylene, diethyl-1,2-phenylene, diisopropyl-1,2-phenylene, 3,5-di-tert-butyl-1,2-phenylene, 3-tert-butyl-5-methoxy-1,2-phenylene, 3-trimethylsilyl-5-tert-butyl-1,2-phenylene, 3,5-di-tert-amyl-1,2-phenylene, 3-trimethylsilyl-5-(2,4,6-trimethylphenyl)-1,2-phenylene, 3-phenyl-5-tert-butyl-1,2-phenylene, 1,2-naphylyl, and substituted variations of 1,2-naphthylyl. Suitable examples of $Ar^3$ and $Ar^4$ in formula IV include, without limitation, phenyl, tolyl, xylyl ethylphenyl, isopropylphenyl 2-tert-butylphenyl, 2,4-dimethylphenyl, 2,4-diethylphenyl, 2,4-diisopropylphenyl, 2,4-di-tert-butylphenyl, 2,4-dimethoxyphenyl, 2,4-di-tert-amylphenyl, 2-tert-butyl-4-methoxyphenyl, 2-trimethylsily-4-tert-butylphenyl, naphthyl and the like.

In a more preferred embodiment of formula I, each M is phosphorus (P) and Q is selected from 2,2'-bisarylenes. In an even more preferred embodiment of formula I, each M is phosphorus (P); Q is selected from 2,2'-bisarylenes; and W is Formula IV. In yet another even more preferred embodiment, each M is phosphorus (P); Q is selected from 2,2'-bisarylenes; W is formula IV; and n is 0.

Most preferably, each M is phosphorus (P); Q is a 2,2'-bisarylene with substitutions on 3,3', or 5,5', or 3,3',5,5' positions; W is formula IV; n is 0; and the composition is represented by formula VI:

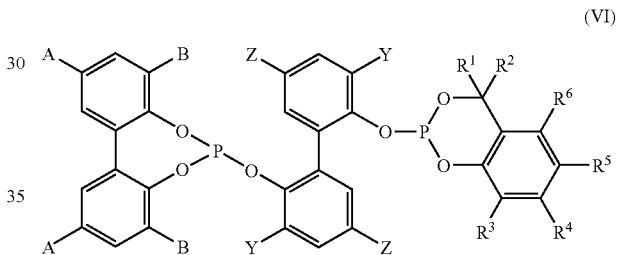

(VI)

wherein $R^1$ and $R^2$ are as defined hereinabove; $R^3$, $R^4$, $R^5$, $R^6$, A and Z are each independently selected from the group consisting of hydrogen, halogen, monovalent hydrocarbyl radicals, alkoxy radicals and tri(hydrocarbyl)silyl radicals, and substituted variations thereof; and B and Y are each independently selected from aryl radicals, tertiary alkyl radicals, and tri(hydrocarbyl)silyl radicals. Preferably, each $R^3$, $R^4$, $R^5$, $R^6$, A and Z is independently selected from the group consisting of hydrogen, halogen (more preferably, chloro, bromo, iodo), alkyl, aryl, alkaryl, aralkyl alicyclic, alkoxy, aryloxy, hydrocarbyl carbonyl [—$C(O)R^7$], hydrocarbyl carboxy [—$OC(O)R^7$] (wherein $R^7$ is a monovalent hydrocarbyl radical), and tri(hydrocarbyl)silyl radicals, and substituted variations thereof. More preferably, the aforementioned hydrocarbyl, alkoxy, and tri(hydrocarbyl)silyl radicals each comprise from 1 to about 20 carbon atoms. Specific illustrative monovalent radicals represented by $R^3$, $R^4$, $R^5$, $R^6$, A and Z include without limitation as alkyl radicals: methyl, ethyl, propyl isopropyl, butyl, sec-butyl t-butyl, neo-pentyl, sec-amyl, t-amyl, iso-octyl, t-octyl, 2-ethylhexyl, iso-nonyl, iso-decyl, and octadecyl; as aryl radicals: phenyl, naphthyl, and anthracyl; as aralkyl radicals: benzyl and phenylethyl; as alkaryl radicals: tolyl xylyl, dimethylphenyls, diethylphenyls, trimethylphenyls, triethylphenyls, and p-alkylphenyls; as alicyclic radicals: cyclopentyl cyclohexyl, cyclooctyl, cyclohexylethyl, and methylcyclohexyl; as alkoxy radicals: methoxy, ethoxy, propoxy, butoxys, and pentoxys; as aryloxy radicals: phenoxy, and naphthoxy; as hydrocarbyl carbonyl radicals: acetyl propionyl, and the like; as hydrocarbyl carboxy radicals: tri(methyl)acetoxy, tri(ethyl)acetoxy, and tri(phenyl)acetoxy; and as tri(hydrocarbyl)silyl radicals: tri(methyl)silyl, tri(ethyl)silyl, and tri(phenyl)silyl. Most preferably, each A is independently selected from hydrogen, chloro, bromo, iodo, methyl, ethyl, tertiary butyl isoamyl tertiary amyl tertiary octyl, methoxy, acetyl [$CH_3C(O)$—], propionyl [$CH_3CH_2C(O)$—] and trimethylacetoxy [$(CH_3)_3C$—$C(O)O$—] radicals. Most preferably, each Z is independently selected from tertiary butyl, tertiary amyl, tertiary octyl tri(methyl)silyl tri(ethyl)silyl, xylyls, dimethylphenyls (more preferably, 2,6-dimethylphenyl), diethylphenyls, trimethylphenyls (more preferably, 2,4,6-trimethylphenyl), and trimethylacetoxy radicals.

The B and Y substituents of formulas VI are each independently selected from aryl radicals, tertiary alkyl radicals, and tri(hydrocarbyl)silyl radicals. Preferably, B and Y are each independently selected from tertiary alkyl radicals, aryl and alkaryl radicals (with the proviso that the aryl radicals do not have substituents on the ortho positions) and tri(hydrocarbyl)silyl radicals, the aforementioned radicals having from 3 to about 30 carbon atoms. Suitable examples of tertiary alkyl radicals include without limitation tertiary butyl, t-amyl, t-octyl, and the like; aryl radicals include phenyl naphthyl, anthracyl, and the like; alkaryl radicals include tolyl xylyl, diethylphenyls, trimethylphenyls, triethylphenyls, p-alkylphenyls, and the like; and tri(hydrocarbyl)silyl radicals include trimethylsilyl, triethylsilyl, triphenylsilyl, triisopropylsilyl, and the like. More preferably, each B is independently selected from tertiary butyl, trimethylsilyl, phenyl, dimethylphenyls (preferably, 3,5-dimethylphenyl), and trimethylphenyls (preferably, 3,4,5-trimethylphenyl radicals. More preferably, each Y is independently selected from tertiary butyl, tertiary amyl, and trimethylsilyl radicals.

Optionally, any of the aforementioned radicals associated with R, $R^1$, $R^2$, $R^3$, $R^4$, $R^5$, $R^6$, A, B, Y, and Z may be substituted, the word "substituted" to include any substituent, that is, halo, nitro, amino, cyano, trifluoromethyl, hydroxy, sulfonyl sulfinyl, and any class of organic substituent (for example, alkyl, aryl, alkoxy, amido, acyl, carbonyloxy, oxycarbonyl, tri(hydrocarbyl)silyl, ether, phosphonyl and thionyl) that is non-interfering with the formula or its catalytic and stabilizing properties.

Most preferably, the ligand composition of this invention is selected from the following species:

Ligand A

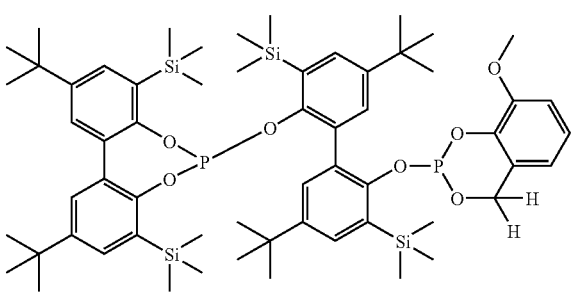

Ligand B

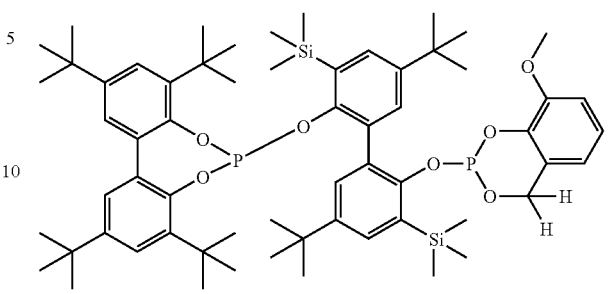

Ligand C

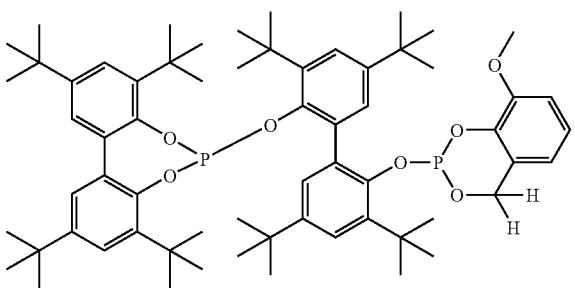

Ligand D

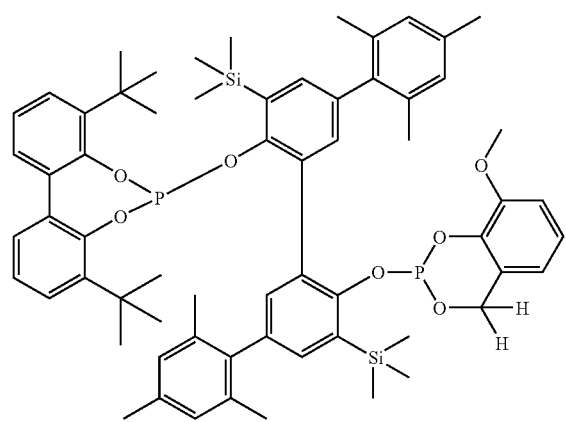

Ligand E

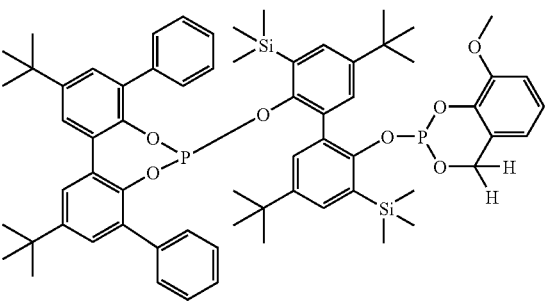

-continued

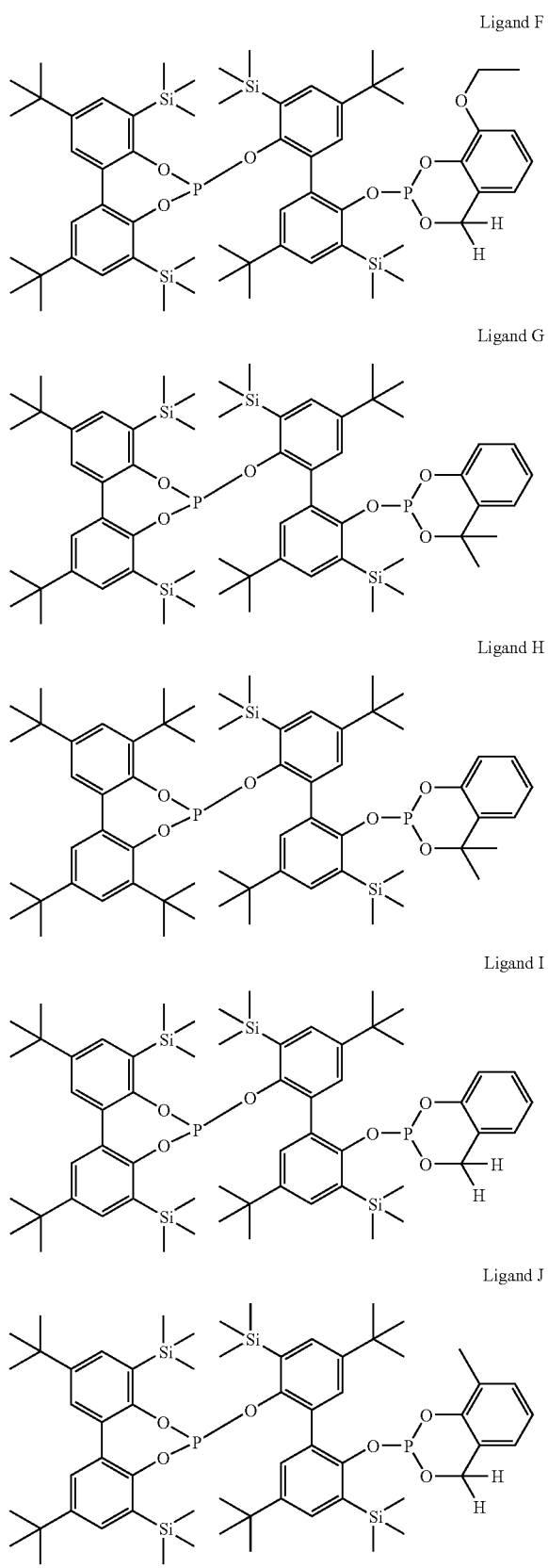

Ligand F

Ligand G

Ligand H

Ligand I

Ligand J

The novel ligand composition of formula I of this invention can be readily synthesized by a process comprising contacting a dichloro-bis-chelating ligand composition represented by formula VII:

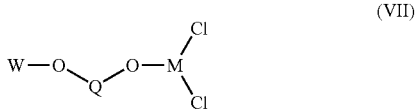

(VII)

with a 2-hydroxybenzyl alcohol of formula VIII:

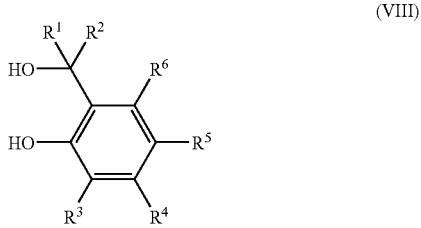

(VIII)

wherein W, Q, M, $R^1$, $R^2$, $R^3$, $R^4$, $R^5$, and $R^6$ are defined hereinbefore in connection with formulas I through VI, the contacting being carried out under reaction conditions sufficient to prepare the ligand composition of Formula I. The preparation of the dichloro-bis chelating starting material of formula VII is well known in the art, as described in EP-A1-569,328, EP-A1-353,770, EP-A1-213,639, and as disclosed by Stephen D. Pastor et al., in *Inorganic Chemistry* (1996), 35(4), 949-958, the aforementioned references being incorporated herein by reference. 2-Hydroxybenzyl alcohols are well known and readily available.

Any quantities of dichloro-bis-chelating compound of formula VII and 2-hydroxybenzyl alcohol of formula VIII can be employed in the synthesis reaction, provided that the novel ligand composition of formula I is produced. Typically, the molar ratio of hydroxybenzyl alcohol of formula VIII to dichloro-bis-chelating compound of formula VII is greater than about 0.7/1. Typically, the molar ratio of hydroxybenzyl alcohol of formula VIII to dichloro-bis-chelating compound of formula VII is less than about 1.3/1. Preferably, the molar ratio of hydroxybenzyl alcohol of formula VIII to dichloro-bis-chelating compound of formula VII is about 1.0/1.0 (within ±15 percent). The condensation reaction is typically conducted in the presence of a solvent, any variety of which may be employed provided that the desired ligand composition of formula I is obtained. Preferably, the solvent is selected to solubilize the bis-chelate and hydroxyalcohol reactants, the hydroxy alcohol in particular. The usual precautions are taken to select a solvent that is non-reactive with the reactants and stable under the synthesis conditions. Ethers, more preferably, tetrahydrofuran, are the preferred solvent. The amount of solvent used may be readily determined by one skilled in the art. Generally, sufficient solvent is employed such that the concentrations of the dichloro-bis-chelating compound of formula VII and the hydroxyalcohol of formula VIII are each no greater than about 20 weight percent, and preferably, no greater than about 10 weight percent in the resulting reaction mixture. Typically, the concentrations of the dichloro-bis-chelating compound of formula VII and the hydroxyalcohol of formula VIII are each greater than about 0.01 weight percent, and preferably, each greater than about 0.1 weight percent, in the reaction mixture.

A base is also employed in the synthesis of the composition of formula I. The base may be any base that is capable of binding hydrogen chloride. Non-limiting examples of suitable bases include amines, such as alkyl amines, preferably, $C_{1-20}$ trialkyl amines, as well as basic N-heterocycles. Non-limiting examples of suitable bases include triethylamine, tripropylamine, tributylamine, and pyridine. Since two equivalents of hydrogen chloride are produced per equivalent of dichloro-bis-chelating compound reacted, the base is typically employed in a two-fold or greater molar excess relative to the moles of dichloro-bis-chelating compound. Preferably, the molar ratio of base to dichloro-bis-chelate is greater than about 2.2/1, but less than about 2.7/1.

Any conventional reactor and operable reaction conditions can be employed for the synthesis, provided that the desired ligand composition of formula I is produced. For example, batch reactors and continuous stirred tank reactors (CSTR) can be suitably employed. The reaction temperature is typically greater than about −35° C. and less than about 60° C. Usually, the reactants are initially mixed at about −30° C., and then the reaction temperature is allowed to rise to ambient temperature, at which temperature the synthesis may be essentially complete. If not complete, then a slight heating up to about 60° C. may be employed. The synthesis is conveniently conducted at ambient pressure; but a higher or lower pressure may also be employed. Usually, the synthesis is conducted under an inert gaseous atmosphere, such as nitrogen, argon, helium, or the like. The residence time of the reactants in the reactor is typically greater than about 15 minutes, and preferably, greater than about 30 minutes. The residence time in the reactor is less than about 10 hours, preferably, less than about 5 hours, more preferably, less than about 3 hours, and most preferably, less than about 2 hours. At the completion of the synthesis, the ligand composition of formula I is isolated from the reaction mixture by methods known to those skilled in the art. Typically, an amine salt, resulting from the reaction of the base with the co-product hydrogen chloride, is filtered off; and the resulting product fluid is treated by standard methods including, for example, evaporation, distillation, crystallization, extraction, or tituration to yield an essentially pure ligand product of formula I. Typically, the in situ (non-isolated) yield of ligand product is greater than about 85 mole percent, preferably, greater than about 95 mole percent. The isolated yield of ligand product is typically greater than about 50 mole percent, preferably, greater than about 60 mole percent, and more preferably, greater than about 70 mole percent.

The composition of formula VII can be prepared by reacting a composition of formula IX:

(IX)

with a Group VB trichloride ($MCl_3$), wherein W, Q, and M are as defined hereinbefore in connection with formula I. Preferably, M is phosphorus, and the Group VB trichloride is phosphorus trichloride ($PCl_3$). Likewise, the composition of formula IX can be prepared by reacting a monochlorodite composition of formula X:

(X)

with a bis-hydroxy compound of formula XI:

(XI)

wherein W and Q are as defined hereinbefore in connection with formula I. The general conditions for the above-described synthesis reactions of formulas VII and IX are similar to the conditions used for making the compound of formula I and are known in the art, as found in U.S. Pat. No. 4,748,261, incorporated herein by reference. The synthesis of the monochlorodite of formula X may also be found in the art. A preferred synthesis of formula X is described in co-pending U.S. patent application Ser. No. 60/363,725, filed on Mar. 11, 2002, wherein $MCl_3$ (M=P, Ar, or Sb) is reacted with a bis-hydroxy compound corresponding to the organic portion of fragment W (organic portion of formulas II, III, IV, and V hereinabove as bis-hydroxy compounds absent M) in the presence of a stoichiometric or excess amount of a weak amine base, such as N,N-dimethylaniline (DMA), under reaction conditions. Typically, about stoichiometric quantities of bis-hydroxy compound $W(OH)_2$, $MCl_3$, and base (1:1:2) are employed; but variations from stoichiometric quantities may be tolerated. Again, ethers, alkanes, and aromatic hydrocarbons provide suitable solvents. Preferably, the solvent is selected from tetrahydrofuran, diethyl ether, toluene, and mixtures thereof. The concentration of the reagents in the solvent ranges in each instance from greater than about 0.01 weight percent, preferably, greater than about 0.1 weight percent to less than about 20 weight percent, and preferably, less than about 10 weight percent. The process typically is conducted at a temperature greater than about −78° C., and preferably, greater than about −40° C. The process is typically conducted at a temperature less than about 60° C., preferably, less than about 40° C. Generally, the process is carried out at ambient pressure, but higher or lower pressures may be also employed. Reaction under an inert atmosphere, such as nitrogen, argon, or helium is preferred.

The composition of this invention of formula I finds a variety of applications including, for example, as a ligand in transition metal complex catalysts and catalyst precursors that are used in carbonylation processes, preferably, hydroformylation processes. Accordingly, in a second aspect this invention provides for an entirely new class of complex catalysts and complex catalyst precursor compositions that comprise a Group VIII transition metal bonded to at least one ligand represented by formula I. Optionally, the Group VIII transition metal may also be bonded to carbon monoxide, hydrogen, or both carbon monoxide and hydrogen. The Group VIII transition metal that makes up the complex catalyst or catalyst precursor composition of this invention includes those transition metals selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, with the preferred metals being ruthenium, rhodium, cobalt, and iridium, more preferably, rhodium and cobalt, and most preferably, rhodium. The term "complex" as used herein shall be taken to mean a coordination compound formed by the union of one or more ligands, herein one or more ligands of formula I, with a Group VIII metal. Inherently, the ligands are electronically rich, since each ligand possesses two Group VB donor atoms, each of which possesses one available or unshared pair of electrons that is capable of forming a coordinate covalent bond independently or in concert (for example, via chelation) with the Group VIII transition metal. The oxidation state of the Group VIII metal may be any available oxidation state, both electronically neutral (zero) or electronically deficient (positive valence) that allows for bonding to the ligand. Moreover, the oxidation state of the Group VIII transition metal as well as the overall oxidation state of the coordination complex or complex precursor may vary during use in the carbonylation process. The number of available coordination sites on the Group VIII transition metal is well known in the art and may range typically from about 4 to about 6. Optionally, the Group VIII transition metal may be additionally bonded to carbon monoxide, hydrogen, or both carbon monoxide and hydrogen.

In a third and related aspect, this invention can be described as a novel transition metal complex catalyst or catalyst precursor solution comprising an organic solvent, a solubilized Group VIII transition metal-ligand complex, and optionally, free ligand, wherein the ligand is represented by formula I hereinabove. Such novel solutions may be prepared by forming a solution comprising an organic solvent, free ligand, and a Group VIII transition metal source material, such as the corresponding transition metal oxide, hydride, carbonyl, salt, or organotransition metal complex described hereinafter; and thereafter subjecting such solution to reaction conditions sufficient to bind at least a portion of the ligand to the Group VIII transition metal. Optionally, carbon monoxide and hydrogen may be dissolved in the solution and bonded to the Group VIII transition metal.

The Group VIII transition metal-ligand complex catalyst of this invention can be synthesized by methods known in the art. For instance, Group VIII transition metal hydridocarbonyl(ligand) catalysts may be preformed and introduced into the reaction medium of a carbonylation process. Standard identification methods may be used to identify the complex catalyst or catalyst precursor composition, including for example, elemental analysis, mass spectroscopy, infrared spectroscopy, and $^1$H, $^{31}$P, and/or $^{13}$C NMR spectroscopy, and the like.

Preferably, the Group VIII transition metal-ligand complex catalyst of this invention is derived from a Group VIII transition metal source material that is introduced into the carbonylation reaction medium for in situ formation of the active catalyst. For example, rhodium source materials, such as, rhodium acetylacetonate, rhodium dicarbonyl acetylacetonate, $Rh_2O_3$, $Rh_4(CO)_{12}$, $[RhCl(CO)_2]_2$, $Rh_6(CO)_{16}$, $Rh(NO_3)_3$, and the like may be introduced into the carbonylation reaction medium along with the ligand for the in situ formation of the active catalyst. In a preferred embodiment, rhodium dicarbonyl acetylacetonate is employed as a rhodium source material and reacted in the presence of a solvent with the ligand to form a rhodium-ligand complex catalyst precursor composition, which is introduced into the reactor along with excess free ligand for the in situ formation of the active catalyst. In any event, it is sufficient for the purpose of this invention to understand that carbon monoxide, hydrogen, and ligand are all ligands that are capable of being complexed with the Group VIII transition metal, for example, rhodium, and that an active Group VIII transition metal-ligand catalyst is present in the reaction medium under the conditions of the carbonylation, and preferably, hydroformylation process. The reaction conditions sufficient for formation of the complex catalyst or catalyst precursor in most cases will be similar to the carbonylation reaction conditions described hereinbelow.

In a preferred embodiment the Group VIII transition metal-ligand complex catalyst composition of this invention may be defined as comprising a Group VIII transition metal complexed with carbon monoxide and at least one ligand of formula I, said ligand being bonded (that is, complexed) to the metal in a chelated or non-chelated fashion. Moreover, the term "comprising" is also meant to include hydrogen complexed with the metal, particularly in the case of rhodium-catalyzed hydroformylation processes wherein hydrogen is also present in the reaction mixture. As noted hereinabove, the carbonyl and/or hydrogen ligands of an active rhodium ligand complex catalyst may be present as a result of being ligands bound to a Group VIII transition metal source material, or as a result of being ligands bound to a Group VIII transition metal complex precursor composition, and/or as a result of in situ formation due to hydrogen and carbon monoxide being employed in the hydroformylation process.

In a fourth aspect, this invention provides for a carbonylation process, which comprises contacting an organic compound capable of being carbonylated with carbon monoxide in the presence of the Group VIII transition metal-ligand complex catalyst mentioned above, wherein the ligand is represented by formula I. Such processes may include the carbonylation of organic compounds, such as olefins, acetylenes, alcohols, and activated chlorides, with carbon monoxide, and optionally, either hydrogen, alcohol, amine, or water, as well as ring closure reactions of functionally unsaturated compounds, for example, unsaturated amides, with carbon monoxide. Exemplary carbonylation processes include, for example, simple carbonylation (insertion of carbonyl in absence of other reactant), hydroformylation, hydroacylation (intermolecular and intramolecular), hydrocyanation, hydroamidation, hydroesterification, and hydrocarboxylation processes. The contacting in such a process is conducted under carbonylation conditions sufficient to prepare the corresponding carbonylated organic compound. In a preferred embodiment, the carbonylation process also contains free ligand in addition to the ligand bonded to the Group VIII transition metal. Preferably, the carbonylation process involves a hydroformylation process, more preferably, the hydroformylation of an olefin with carbon monoxide in the presence of hydrogen to prepare an aldehyde. The more preferred carbonylation process to prepare aldehydes is known in industry under varying names including the "oxo" process, the "oxo" reaction, "oxonation," the "Roelen reaction," or more commonly, simply "hydroformylation." The processing techniques employed in the carbonylation process of this invention correspond to any of the known processing techniques employed in conventional carbonylation processes, or hydroformylation processes, as described in detail hereinafter.

It is to be noted that the successful practice of this carbonylation process invention does not depend and is not predicated upon the exact formula of the catalytically active metal complex species, which may be present in a mononuclear, dinuclear, or higher nuclearity form. Indeed, the exact formula of the catalytically active metal ligand complex may be difficult to determine analytically. Although not intended to be bound to any theory or mechanistic discourse, it appears that the active catalytic species in its general form comprises the Group VIII transition metal in complex combination with one or more ligands of formula I, further in combination with carbon monoxide, since carbon monoxide is also present and capable of complexing to the Group VIII transition metal. As noted previously, the ultimate composition of the active complex may also contain one or more additional ligands, such as hydrogen, or an anion satisfying the coordination sites or nuclear charge of the Group VIII transition metal, as the case may be, obtained typically from the starting transition metal material. Illustrative additional ligands include halogen ($Cl^-$, $Br^-$, $I^-$), alkyl, aryl, substituted aryl, $CF_3^-$, $C_2F_5^-$, $CN^-$, $R'_2PO^-$, $R'P(O)(OH)O^-$ (wherein each R' is alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2=CHCH_2^-$, $C_6H_5CN$, $CH_3CH=$, NO, $NH_3$, pyridine, $(C_2H_5)_3N$, monoolefins, diolefins, triolefins, tetrahydrofuran, and the like. Of course, it is to be understood that the active complex species is preferably free of any additional organic ligand or anion that might poison the catalyst and have an undue adverse effect on the catalyst performance. For instance, in conventional rhodium-catalyzed hydroformylation processes, halogen atoms and sulfur atoms may typically poison the catalyst. Accordingly, it is preferred that in the rhodium-catalyzed hydroformylation reaction of this invention that the active catalyst also be free of halogen and sulfur directly bonded to the rhodium, although such requirement may not be absolutely necessary.

Any amount of complex catalyst can be employed in the carbonylation reaction medium, provided that the amount is sufficient to catalyze the desired carbonylation process. In general, the concentration of complex catalyst provides for a concentration of Group VIII transition metal of greater than about 10 parts per million (ppm), preferably, greater than about 25 ppm, by weight calculated as free metal Generally, the concentration of complex catalyst provides for a concentration of Group VIII transition metal of less than about 1,000 ppm, preferably, less than about 800 ppm, and more preferably, less than about 600 ppm, by weight calculated as free metal.

The olefinic reactants to be used in the preferred carbonylation process of this invention can be any terminally or internally olefinically-unsaturated aliphatic hydrocarbon, including straight chain, branched chain, and cyclic formulas. Such olefins contain preferably from 2 to about 60 carbon atoms and one or more unsaturated groups. Moreover, such olefins may contain substituents that essentially do not adversely interfere with the hydroformylation process, including, for example, carbonyl, carbonyloxy, hydroxy, oxycarbonyl, halo, alkyoxy, aryl haloalkyl, and the like. Non-limiting examples of suitable olefinic unsaturated reactants include, for example, alpha olefins, internal olefins, alkyl alkenoates, alkenyl alkanoates, alkenyl alkyl ethers, alkenols, and the like; more specifically, ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethylhexene, styrene, 3-phenyl-1-propene, butadiene, 1,3-cyclohexadiene, 1,4-cyclohexadiene, 1,7-octadiene, 3-cyclohexyl-1-butene, allyl alcohol, hex-1-en-4-ol, oct-1-ene-4-ol, vinyl acetate, allyl acetate, 3-butenyl acetate, vinyl propionate, 1-vinyl-3-cyclohexene, allyl propionate, allyl butyrate, methyl methacrylate, 3-butenyl acetate, vinyl ether, vinyl methyl ether, allyl ethyl ether, n-propyl-7-octenoate, methyl 1-decenoate, 3-butenenitrile, 5-hexenamide, methyl oleate, castor oil, soybean oil and the like. Mixtures of olefinic starting materials can be employed, if desired. Preferably, the carbonylation process is especially useful for the production of aldehydes by the hydroformylation of alpha olefins containing from 2 to about 60 carbon atoms and internal olefins containing from 4 to about 50 carbon atoms, as well as mixtures of such alpha and internal olefins.

The carbonylation process, and preferably hydroformylation process, of this invention is also preferably conducted in the presence of an organic solvent for the Group VIII transition metal complex catalyst. Any suitable solvent that does not unduly interfere with the carbonylation process can be used including those types of solvents commonly used in prior art carbonylation processes. By way of illustration, suitable solvents for rhodium catalyzed hydroformylation processes include those disclosed, for example, in U.S. Pat. No. 3,527,809; U.S. Pat. No. 4,148,830; and U.S. Pat. No. 5,929,289, the aforementioned citations being incorporated herein by reference. Non-limiting examples of suitable solvents include saturated hydrocarbons, aromatic hydrocarbons, ethers, aldehydes, ketones, nitriles, and aldehyde condensation products. More specific solvents, for example, include the following solvents: tetraglyme, pentanes, cyclohexane, benzene, xylene, toluene, diethyl ether, tetrahydrofuran, butyraldehyde, and benzonitrile. Mixtures of two or more solvents may also be employed. In rhodium catalyzed hydroformylation processes, it may be preferred to employ as the primary solvent aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486, incorporated herein by reference. Indeed, while one may employ, if desired, any suitable solvent at the start-up of a continuous process, the primary solvent will normally eventually comprise both aldehyde products and higher boiling aldehyde liquid condensation by-products, due to the nature of such continuous processes. The amount of solvent is not especially critical and need only be sufficient to provide the reaction medium with the desired amount of Group VIII transition metal concentration. Typically, the amount of solvent ranges from about 5 percent to about 95 percent by weight, based on the total weight of the reaction medium.

The carbonylation process of this invention may preferably be conducted in the presence of free ligand, that is, ligand that is not complexed with the Group VIII transition metal. The use of free ligand may not be absolutely necessary, however. The free ligand may correspond to any of the ligand species illustrated hereinabove. While it is preferred to employ a free ligand that is the same as the ligand complexed to the transition metal in the Group VIII-ligand complex catalyst, it is not absolutely required for the free and complexed ligands to be the same. The free and complexed ligands may be different, if desired. Prior art triorganophosphines, triorganophosphites, diorganophosphites, and bisphosphites may be employed as the free ligand. While the carbonylation process of this invention may be carried out in any excess amount of free ligand, typically at least one mole of free ligand per mole of Group VIII transition metal is present in the reaction medium. For most purposes, preferably, the amount of ligand per mole of Group VIII transition metal is greater than about 1.1/1, more preferably, greater than about 1.3/1 is employed. Preferably, the amount of ligand per mole of Group VIII transition metal is less than about 100/1, more preferably, less than about 50/1. The aforementioned ratios correspond to the sum of both the free and complexed ligand. Make-up ligand can be added during the carbonylation process at any time and in any suitable manner, so as to maintain a predetermined concentration of free ligand in the reaction medium.

The reaction conditions for effecting carbonylation can be chosen from any of those conditions conventionally used and known for such processes. Generally, the carbonylation process temperature is greater than about 30° C., preferably, greater than about 40° C. Generally, the carbonylation process temperature is less than about 200° C., preferably, less than about 120° C. Pressures greater than about 1 psia (7 kPa) to less than about 10,000 psia (68,948 kPa) are usually employed. The carbonylation process may be conducted as a single pass, continuous process. Alternatively, the carbonylation process may include recycle of any unreacted olefin reagent for multiple pass, continuous processing.

As noted herein, the preferred carbonylation process involves contacting an olefin with carbon monoxide and hydrogen under reaction conditions sufficient to prepare an aldehyde. The total gas pressure of hydrogen, carbon monoxide, and olefinic unsaturated reactant in the hydroformylation process may range from greater than about 1 psia (7 kPa) to less than about 10,000 psia (68,948 kPa). Preferably, the total pressure of hydrogen, carbon monoxide, and olefinic unsaturated reactant is less than about 2000 psia (13,790 kPa), and more preferably, less than about 1500 psia (10,342 kPa). More specifically, the carbon monoxide partial pressure of the hydroformylation process of this invention is typically greater than about 1 psia (7 kPa), preferably, greater than about 3 psia (21 kPa). The carbon monoxide partial pressure of the hydroformylation process of this invention is typically less than about 1000 psia (6,8948 kPa), preferably, less than about 750 psia (5171 kPa). The hydrogen partial pressure is typically greater than about 5 psia (35 psia), preferably, greater than about 10 psia (69 kPa). The hydrogen partial pressure is typically less than about 1000 psia (6,8948 kPa), preferably, less than about 750 psia (5171 kPa). In general, the $H_2$/CO molar ratio of gaseous hydrogen to carbon monoxide may be greater than about 1/10, and preferably, equal to or greater than about 1/1. The $H_2$/CO molar ratio may be less than about 100/1, and preferably, equal to or less than about 10/1.

Further to the hydroformylation process of this invention, the reaction temperature will depend upon the particular olefinic reagent and metal catalyst employed, as well as the efficiency desired. Generally, hydroformylations at reaction temperatures of greater than about 30° C., and preferably, greater than about 40° C., are suitable. Generally, hydroformylations at reaction temperatures of less than about 150° C., and preferably, less than about 120° C., are suitable. Alpha-olefins are more preferably hydroformylated at a temperature of greater than about 40° C. and less than about 80° C.; whereas less reactive olefins, such as isobutylene and internal olefins, are more preferably hydroformylated at a temperature greater than about 50° C. and less than about 120° C.

The carbonylation process, and preferred hydroformylation process, of this invention can be carried out in the liquid or gas phase, or preferably, in mixed liquid and gas phases, which can more preferably involve a continuous liquid phase and a gas phase recycle system or combination of recycle systems. In a preferred embodiment, the process involves a continuous homogeneous catalysis process wherein carbonylation is carried out in the presence of free ligand and any conventional solvent, as described hereinabove.

Optionally, the hydroformylation process may be conducted in the presence of an amine base, which functions apparently to scavenge acid by-products, although the invention should not be limited to such a theory. The amine base may be any alkyl or aryl amine or mixture thereof, provided that the amine so selected does not interfere with the hydroformylation process. Suitable amine bases include N,N-di(isopropy)ethylamine, triethylamine, N,N-di(methyl)aniline, and pyridine. A preferred amine base has a $pK_b$ of less than 8.9. A more preferred base is N,N-di(isopropyl)ethylamine.

In the preferred hydroformylation process of this invention, the olefin conversion is generally greater than about 70 mole percent. For the purposes of this invention, "olefin conversion" shall be defined as the mole percentage of olefin feed converted to all products. Olefin conversion will vary depending upon the specific olefin reactant, the specific form of the catalyst, and the specific process conditions employed. Preferably, the olefin conversion is greater than about 80 mole percent, more preferably, greater than about 90 mole percent, and most preferably, greater than about 95 mole percent.

Likewise, in the preferred hydroformylation process of this invention, the yield of aldehyde product, for example, n-nonanal, achieved is generally greater than about 70 mole percent. For the purposes of this invention, "yield" will be defined as the mole percentage of aldehyde product produced, based on the total moles of olefin fed to the process. Again, the yield of aldehyde produced will vary based on the specific olefin reactant, the specific form of the catalyst, and the specific process conditions employed. Preferably, the yield of aldehyde is greater than about 75 mole percent, more preferably, greater than about 80 mole percent, even more preferably, greater than about 85 mole percent, and most preferably, greater than about 90 mole percent.

An additional advantage of the process of this invention resides in the high molar ratio of normal (linear) to iso (branched) (N:I) aldehyde products achieved, when normal aldehydes are the desired products. Typically, the N:I molar ratio is greater than about 10:1, preferably, greater than about 20:1, more preferably, greater than about 30:1, and most preferably, greater than about 40:1. In some instances, an N:I molar ratio of greater than 100:1 is observed. The process of this invention also exhibits acceptable rates of reaction (typically, equal to or greater than about 2 moles per hour (M/h), and preferably, greater than about 10 Mph), and desirably low selectivities to isomerization products and hydrogenated products (typically, less than about 10 mole percent, and preferably, less than about 5 mole percent).

Finally, the aldehyde products of the hydroformylation process have a wide range of utilities that are well known and documented in the prior art; for example, they are especially useful as starting materials for the production of alcohols and acids.

The following examples are illustrative of the present invention and are not to be regarded as limiting thereof. Variations in operational parameters, such as reactants, process conditions, forms of the transition metal ligand complex catalyst, and ligand species, which all fall within the scope of the claims, will be apparent to those skilled in the art based on the description and examples contained herein. All of the parts, percentages, and proportions are given by mole percent, unless otherwise indicated.

EXAMPLE 1

Synthesis of Ligand A

The following procedure was used to prepared Ligand A having the formula:

Ligand A

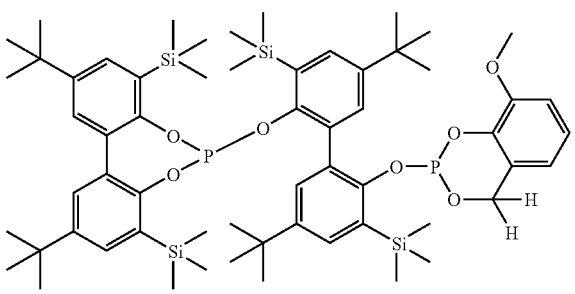

At the start, a precursor compound designated "TMS-TMS-PCl$_2$" was prepared having the formula:

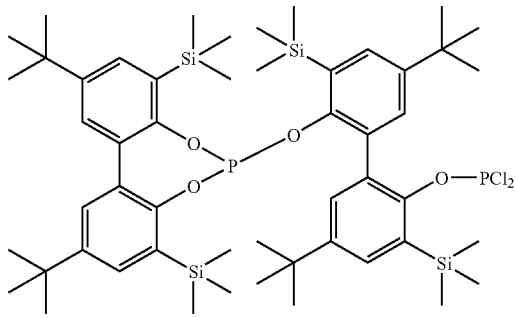

in accordance with the following procedure.

To a cold (−30° C.) solution of tetrahydrofuran (20 ml) and 3,3'-bis(trimethylsilyl)-5,5'-di-t-butyl-2,2'-biphenol (TMS-diol, 6.00 g, 13.6 mmol) was added with stirring triethylamine (2.80 g, 27.7 mmol) and phosphorus trichloride (PCl$_3$) (0.933 g, 6.80 mmol). A white precipitate formed immediately, and the slurry was stirred and refluxed for 4 hours. The resulting amine chloride salt was filtered off and washed with tetrahydrofuran. The filtrate was cooled to −30° C. To this cold solution was added PCl$_3$ (1.50 g, 10.9 mmol) and triethylamine (1.4 g, 13.9 mmol) with stirring. A white precipitate formed immediately. The mixture was stirred for 2 hours at room temperature and then filtered to remove the amine salt. The filtrate was evaporated to yield a white solid, which was triturated in acetonitrile and filtered to produce essentially pure TMS-TMS-PCl$_2$ (6.02 g; 87.6%) $^{31}$P{$^1$H} NMR (122 MHz, CDCl$_3$, δ, ppm): Major diastereomer (92%): 142.62 and 204.42 (d, J$_{P-P}$=3 Hz); Minor diastereomer (8%): 142.43 and 203.34 (s).

Next, a cold (−30° C.) solution containing tetrahydrofuran (5.0 ml), 2-hydroxy-3-methoxybenzyl alcohol (0.173 g, 1.09 mmol), and triethylamine (0.25 g, 2.5 mmol) was added to a stirred cold (−30° C.) solution comprising tetrahydrofuran (5.0 ml) and TMS-TMS-PCl$_2$ (1.00 g, 0.986 mmol). The resulting mixture was stirred for 1 hour, during which time the mixture was warmed to ambient temperature (about 22° C.). The mixture was then filtered to remove triethylamine hydrochloride salt, and the filtrate was evaporated to obtain a white solid. The while solid was triturated in acetonitrile to obtain pure Ligand A as a white powder. Yield 0.875 g (81.0%). $^{31}$P{$^1$H} NMR (122 MHz, CDCl$_3$, δ, ppm) showed four diastereomers: diastereomer 1 (79%): 112.3 and 143.1 (s); diastereomer 2 (17%): 109.7 and 144.0 (s); diastereomer 3 (3%): 113.0 and 142.8 (s); and diastereomer 4 (1%): 111.2 and 143.3 (s).

EXAMPLE 2

Synthesis of Ligand D

The following procedure was followed to prepare Ligand D having the formula:

Ligand D

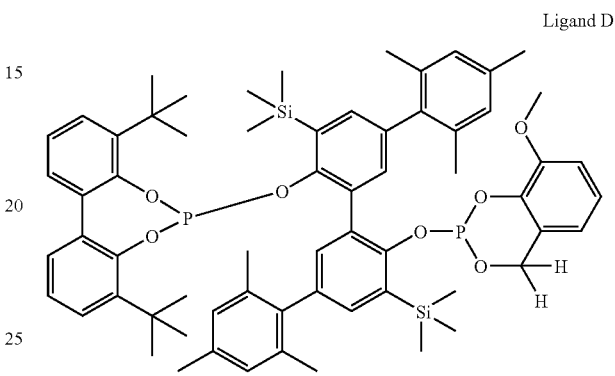

At the start, a precursor compound designated "TB-MesTMS-PCl$_2$" was prepared having the formula:

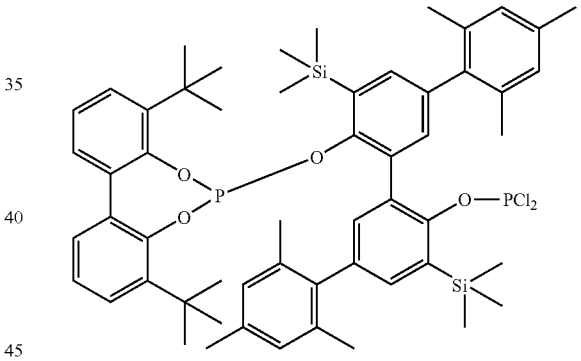

in accordance with the following procedure:

3,3'-Di-t-butyl-1,1'-biphenyl phosphorochloridite (TB-PCl) was prepared according to a procedure described in U.S. Pat. No. 4,748,261. To a cold (−30° C.) solution containing tetrahydrofuran (10.0 ml) and TB-PCl (1.508 g, 4.134 mmol) was added with stirring a cold (−30° C.) solution containing tetrahydrofuran (10.0 ml) and 3,3'-bis(trimethylsilyl)-5,5'-bis(2,4,6-trimethylphenyl)-2,2'-biphenol (MesTMS-diol) (2.344 g, 4.134 mmol) and triethylamine (0.418 g, 4.134 mmol). After stirring the reaction mixture for 1 hour at room temperature, triethylamine (0.6312 g, 6.25 mmol) was added to the reaction mixture. After cooling the mixture to −30° C., PCl$_3$ (0.8521 g, 6.205 mmol) in tetrahydrofuran (5.0 ml) was added. The reaction mixture was stirred for 10 hours at room temperature, and an amine salt was filtered and washed with ether. The filtrate was then evaporated to yield a white solid, which was further dried under high vacuum for 30 min. The crude white solid was triturated in acetonitrile (15 ml) for 1 hour and essentially pure product was collected by filtration and dried under vacuum. Yield: TB-MesTMS-PCl$_2$ (3.56 g, 87%). $^{31}$P NMR (122 MHz, δ, ppm): Diastereomer 1 (94%): 139.28 and 203.93 (d, J$_{P-P}$=5 Hz); Diastereomer 2 (6%): 140.69 and 202.93 (s).

Next, Ligand D was synthesized by reacting TB-MesTMS-PCl$_2$, 2-hydroxy-3-methoxybenzyl alcohol, and triethylamine in a manner similar to the preparation of Ligand A hereinabove. Yield Ligand D: 70%. $^{31}$P NMR (122 MHz, δ, ppm): Diastereomer 1 (84%): 113.52, 138.87 (d, J$_{P-P}$=5.1 Hz); Diastereomer 2 (7%): 110.22, 138.87 (d, J$_{P-P}$=15 Hz); Diastereomer 3 (5%): 114.40, 141.13; Diastereomer 4 (4%): 113.51, 140.50.

EXAMPLE 3

Synthesis of Ligand E

Ligand E having the following formula was prepared as follows.

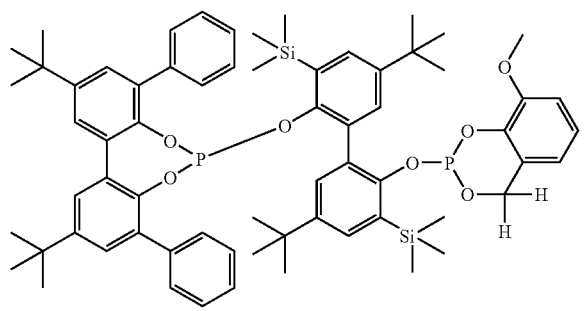

At the start, a precursor compound designated "o-PhB-TMS-PCl$_2$" was prepared having the formula.

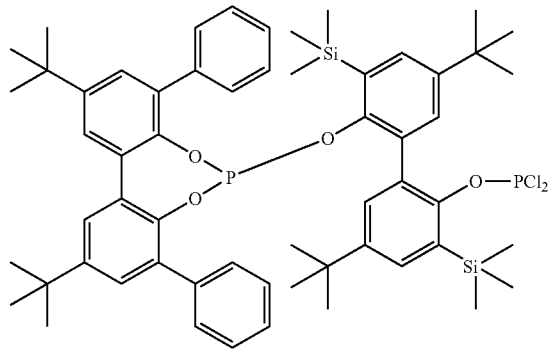

To a cold (−30° C.) solution containing tetrahydrofuran (THF) (40 ml), diethyl ether (80 ml), 3,3'-diphenyl-5,5'-di-t-butyl-2,2'-biphenol (2.9093 g, 6.456 mmol), and N,N-dimethylaniline (1.6434 g, 13.561 mmol) was added with stirring a cold (−30° C.) solution containing diethyl ether (10 ml) and PCl$_3$ (0.9312 g, 6.781 mmol). After stirring the mixture for one hour at ambient temperature, an N,N-dimethylaniline hydrochloride salt was filtered and washed with ether. The filtrate was evaporated under vacuum to yield a white solid, which was triturated in acetonitrile (15 ml) for 2 hours, filtered and dried. Yield of 3,3'-diphenyl-5,5'-di-t-butyl-2,2'-biphenyl phosphorochloridite (oPhB-PCl): 2.89 g, 87%. $^{31}$P NMR (122 MHz, CDCl$_3$, δ): 176.80 ppm.

To a cold (−30° C.) solution of tetrahydrofuran (5 ml) and oPhB-PCl (1.40 g, 2.72 mmol) was added quickly a cold (−30° C.) solution of tetrahydrofuran (5 ml), 3,3'-bis(trimethylsilyl)-5,5'-di-t-butyl-2,2'-biphenol (TMS-diol) (1.24 g, 2.72 mmol), and triethylamine (0.27 g, 2.72 mmol). After stirring for one hour at room temperature, a $^{31}$P NMR sample was taken and NMR data was acquired immediately. The spectrum showed ~98% consumption of oPhB-PCl. The intermediate oPhB-TMS-OH was used in situ for the next step after removing the triethylamine hydrochloride salt by filtration. To the cold (−30° C.) solution of oPhB-TMS-OH was added PCl$_3$ (0.45 g, 3.27 mmol) and then triethylamine (NEt$_3$) (0.33 g, 3.26 mmol). The mixture was stirred for one hour at room temperature. A $^{31}$P NMR sample was taken and the NMR data was acquired immediately. The $^{31}$P NMR sample showed the reaction was complete. The triethylamine hydrochloride salt was filtered off and washed with ether. The filtrate was evaporated. The resulting solid residue was triturated in acetonitrile, and a product was collected by filtration and dried under vacuum for 30 min. Yield o-PhB-TMS-PCl$_2$: 2.089 g, 75%. $^{31}$P NMR (122 MHz, CDCl$_3$, δ): Diastereomer 1 (94%): 134.92 and 203.85 (d, J$_{P-P}$=14 Hz); Diastereomer 2 (6%): 141.16 and 203.33 (s).

Next, Ligand E was synthesized by reacting oPhB-TMS-PCl$_2$, 2-hydroxy-3-methoxybenzyl alcohol and triethylamine in a manner similar to the preparation of Ligand A hereinabove. Yield Ligand E: 75% percent. $^{31}$P{$^1$H} NMR (122 MHz, CDCl$_3$, δ, ppm) diastereomer 1 (65%): 110.6 and 135.0 (s); diastereomer 2 (32%): 110.5 and 132.5 (d, J$_{P-P}$=63 Hz); diastereomer 3 (3%): 112.9 and 142.2 (s).

EXAMPLE 4

Ligands A and D from Examples 1 and 2, respectively, were each evaluated in the hydroformylation of 1-octene to nonanals, in accordance with the following general procedure. A Parr pressure reactor was loaded with tetrahydrofuran and tetraglyme (1:1 volume ratio), rhodium dicarbonyl acetylacetonate [Rh(CO)$_2$(acac)], the synthesized ligand, and an amine, specifically, N,N-di(isopropyl)ethylamine. The reactor was pressurized with carbon monoxide and hydrogen to the desired partial pressures, and then the contents were heated for 30 minutes to generate the hydroformylation catalyst. Olefin was added through a cylinder pressurized at the reaction pressure. Samples were taken throughout the reaction for gas chromatographic analysis. The process conditions and results of the hydroformylation processes are given in Table 1.

TABLE 1

Hydroformylation of 1-Octene to Nonanals

| Ligand | L/Rh (mole ratio) | n-Nonanal (mol %) | i-Nonanal (mol %) | Isomerization (mol %)[3] | Initial Rate (M/hr) |
|---|---|---|---|---|---|
| A[1] | 1.3/1 | 92.9 | 1.7 | 5.4 | 4.0 |
| A[2] | 1.3/1 | 93.9 | 2.4 | 3.7 | 1.8 |
| D[1] | 1.5/1 | 90.7 | 0.8 | 8.5 | 18 |

[1]Process Conditions: [1-Octene]$_0$ = 1 M; [Rh] = 300 ppm; 50° C.; 3.4 atm (342 kPa) CO; 3.4 atm (342 kPa) H$_2$; CO/H$_2$ molar ratio = 1/1; 20 mole equivalents of N,N-di(isopropyl)ethylamine/mole ligand.
[2]Process Conditions: [1-Octene]$_0$ = 1 M; [Rh] = 300 ppm; 46° C.; 4.1 atm (410 kPa) CO; 2.7 atm (410 kPa) H$_2$; CO/H$_2$ molar ratio = 1.5/1; 20 mole equivalents of N,N-di(isopropyl)ethylamine/mole ligand.
[3]The sum of trans/cis-2-octene, trans/cis-3-octene, and trans/cis-4-octene.

From Table 1 it is seen that bis-chelating compositions A and D function as ligands in rhodium complex catalysts in the hydroformylation of 1-octene to nonanals. The catalysts show high selectivity for the normal isomer (n-nonanal); whereas the branched isomer (i-nonanal) is produced in low yield. The selectivity to isomerized products is also low. The activity of the catalyst formed with ligand D is nearly five times higher than that formed with ligand A.

EXAMPLE 5

A hydroformylation process was conducted in a manner closely similar to Example 4 hereinabove, with the exception that Ligand E was used to hydroformylate 1,3-cyclohexadiene. Process conditions and results are shown in Table 2.

TABLE 1

Hydroformylation of 1,3-Cyclohexadiene (CHD)[1,2]

| Ligand | L/Rh (mole ratio) | 1,2,3,4-THBA (mol %) | Initial Rate (M/hr) |
|--------|-------------------|----------------------|---------------------|
| E      | 1.2/1             | 97                   | 16                  |

[1]Process Conditions: $[1,3\text{-CHD}]_0$ = 2.5 M; [Rh] = 500 ppm; 80° C.; 10 atm (1006 kPa) CO; 10 atm (1006 kPa) $H_2$; $CO/H_2$ molar ratio, 1/1.
[2]1,2,3,4-THBA = 1,2,3,4-tetrahydrobenzaldehyde, which was the initial product, which was further hydroformylated to dialdehydes and also isomerized to 1,2,3,6-tetrahydrobenzaldehyde and 2,3,4,5-tetrahydrobenzaldehyde.

From table 5, it is seen that bis-chelating composition E is capable of functioning as a ligand in a rhodium complex catalyst in the hydroformylation of 1,3-cyclohexadiene to 1,2,3,4-tetrahydrobenzadehyde.

What is claimed is:
1. A bis-chelating ligand composition having the generic formula:

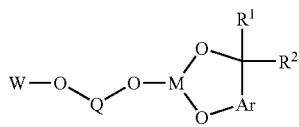

wherein M is a Group VB element selected from phosphorus (P), arsenic (As), or antimony (Sb); $R^1$ and $R^2$ are each independently selected from hydrogen and monovalent hydrocarbyl radicals; or alternatively, $R^1$ and $R^2$ are bonded together to form a hydrocarbyl or substituted hydrocarbyl diradical that taken with the methylene carbon of formula I forms a cyclic or heterocyclic ring; or alternatively, one of $R^1$ or $R^2$ is hydrogen or a monovalent hydrocarbyl radical, while the other of $R^1$ or $R^2$ is a hydrocarbyl or substituted hydrocarbyl radical bonded to an atom in the aryl group Ar to form a cyclic or heterocyclic ring; Ar is selected from 1,2-arylenes; Q is selected from the group consisting of 1,2-arylenes, 2,2'-bisarylenes and alkyl diradicals; and W is selected from the group consisting of Group VB element-containing formulas II, III, IV, and V:

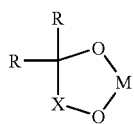

(II)

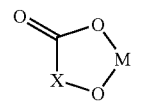

(III)

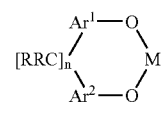

(IV)

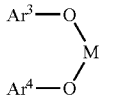

(V)

wherein M is as defined hereinbefore; each R is independently selected from monovalent hydrocarbyl radicals; X is selected from alkyl and aryl diradicals; $Ar^1$ and $Ar^2$ are each independently selected from 1,2-arylenes; $Ar^3$ and $Ar^4$ are each independently selected from monovalent aryl radicals; and n in formula IV is 0 or 1.

2. The composition of claim 1 wherein each M is phosphorus (P).

3. The composition of claim 1 wherein each $R^1$ and $R^2$ is selected from hydrogen, $C_{1\text{-}20}$ primary alkyl radicals, and substituted $C_{1\text{-}20}$ primary alkyl radicals; or wherein $R^1$ and $R^2$ are bonded together to form a diradical that taken with the methylene carbon of formula I forms a $C_{3\text{-}8}$ cyclic or heterocyclic ring.

4. The composition of claim 1 wherein Ar is a $C_{6\text{-}20}$ 1,2-arylene or a substituted derivative thereof.

5. The composition of claim 4 wherein Ar is selected from the group consisting of 1,2-phenylene, 1,2-naphthylene, and 2,3-naphthylene, 3-methyl-1,2-phenylene, 3-ethyl-1,2-phenylene, isopropyl-1,2-phenylene, 3,5-dimethyl-1,2-phenylene, 3,5-diethyl-1,2-phenylene, 3,5-diisopropyl-1,2-phenylene, 3-methyl-1,2-naphthylene, and 1-methyl-2,3-naphthylene.

6. The composition of claim 1 wherein Q is selected from the group consisting of $C_{6\text{-}20}$ 1,2-arylenes, $C_{12\text{-}30}$ 2,2'-bisarylenes, and $C_{1\text{-}20}$ alkyl diradicals, and substituted derivatives thereof.

7. The composition of claim 1 wherein Q is selected from the group consisting of 2,2'-biphenyl, 3,3'-di-tert-butyl-2,2'-biphenyl, 3,3'-bis(trimethylsilyl)-5,5'-di-tert-butyl-2,2'-biphenyl, 3,3',5,5'-tetra-tert-butyl-2,2'-biphenyl, 3,3'-di-tert-butyl-5,5'-dimethoxy-2,2'-biphenyl, 3,3',5,5'-tetra-tert-amyl-2,2'-biphenyl, 3,3'-di-phenyl-5,5'-di-tert-butyl-2,2'-biphenyl, 3,3'-di-tert-butyl-5,5'-bis(trimethylsilyl)-2,2'-biphenyl, 3,3'-bis(trimethylsilyl)-5,5'-bis(2,4,6-trimethylphenyl)-2,2'-biphenyl, ethylene ($-CH_2CH_2-$), 1,3-propylene ($-CH_2CH_2CH_2-$), 1,2-phenylene ($-C_6H_4-$), 1,2-naphthylene ($-C_{10}H_6-$), 2,3-naphthylene ($-C_{10}H_6-$), 3,5-dichloro-1,2-phenylene, 3,5-dibromo-1,2-phenylene, 3-iodo-5-methyl-1,2-phenylene, 3,5-diisopropyl-1,2-phenylene, 3,5,6-trichloro-1,2-phenylene, 3-phenyl-1,2-phenylene, 1,1-diethyl-1,1-methylene, 1,1-cyclohexylidene, 1,1-cycloheptylidene, and 3-isopropyl-6-methyl-1,2-phenylene.

8. The composition of claim 1 wherein each R is independently selected from hydrogen and $C_{1\text{-}20}$ monovalent primary alkyl radicals.

9. The composition of claim 1 wherein X is selected from the group consisting of $C_{1\text{-}20}$ alkyl diradicals, $C_{6\text{-}20}$ aryl diradicals, and substituted derivatives thereof.

10. The composition of claim 1 wherein X is selected from the group consisting of methylene (—CH$_2$—), ethylene (—CH$_2$CH$_2$—), 1,3-propylene (—CH$_2$CH$_2$CH$_2$—), 1,2-phenylene (—C$_6$H$_4$—), 1,2-naphthylene , (—C$_{10}$H$_6$—), 2,3-naphthylene (—C$_{10}$H$_6$—), 3,5-dichloro-1,2-phenylene, 3,5-dibromo-1,2-phenylene, 3-iodo-5-methyl-1,2-phenylene, 3,5-diisopropyl-1,2-phenylene, 3,5,6-trichloro-1,2-phenylene, 3-phenyl-1,2-phenylene, 1,1-diethyl-1,1-methylene, 1,1-cyclohexylidene, 1,1-cycloheptylidene, and 3-isopropyl-6-methyl-1,2-phenylene.

11. The composition of claim 1 wherein Ar$^1$ and Ar$^2$ in formula IV are each independently selected from the group consisting of C$_{6-20}$ 1,2-arylenes and substituted derivatives thereof.

12. The composition of claim 1 wherein Ar$^1$ and Ar$^2$ in formula IV are each independently selected from the group consisting of 1,2-phenylene, methyl-1,2-phenylene, ethyl-1, 2-phenylene, isopropyl-1,2-phenylene, 5-tert-butyl-1,2-phenylene, dimethyl-1,2-phenylene, diethyl-1,2-phenylene, diisopropyl-1,2-phenylene, 3,5-di-tert-butyl-1,2-phenylene, 3-tert-butyl-5-methoxy-1,2-phenylene, 3-trimethylsilyl-5-tert-butyl-1,2-phenylene, 3,5-di-tert-amyl-1,2-phenylene, 3-trimethylsilyl-5-(2,4,6-trimethylphenyl)-1,2-phenylene, 3-phenyl-5-tert-butyl-1,2-phenylene, 1,2-naphthylyl and substituted variations of 1,2-naphthylyl.

13. The composition of claim 1 wherein Ar$^3$ and Ar$^4$ in formula V are each independently selected from the group consisting of C$_{6-20}$ monovalent radicals and substituted derivatives thereof.

14. The composition of claim 1 wherein Ar$^3$ and Ar$^4$ in formula V are each independently selected from the group consisting of phenyl, tolyl, xylyl, ethylphenyl, isopropylphenyl, 2-tert-butylphenyl, 2,4-dimethylphenyl, 2,4-diethylphenyl, 2,4-diisopropylphenyl, 2,4-di-tert-butylphenyl, 2,4-dimethoxyphenyl, 2,4-di-tert-amylphenyl, 2-tert-butyl-4-methoxyphenyl, 2-trimethylsilyl-4-tert-butylphenyl, and naphthyl.

15. The composition of claim 1 wherein each M is phosphorus and Q is a 2,2'-bisarylene, and wherein optionally, W is Formula IV.

16. The composition of claim 15 wherein each M is phosphorus; Q is a 2,2'-bisarylene; W is selected from formula IV; and n is 0, the composition being represented by the following formula:

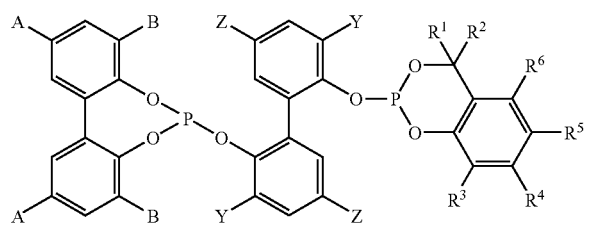

wherein R$^1$ and R$^2$ are each independently selected from hydrogen and primary alkyl radicals, or wherein R$^1$ and R$^2$ are bonded together to form a diradical that together with the methylene carbon of formula I forms a cyclic or heterocyclic ring; R$^3$, R$^4$, R$^5$, R$^6$, A and Z are each independently selected from the group consisting of hydrogen, halogen, monovalent hydrocarbyl radicals, alkoxy radicals and tri(hydrocarbyl)silyl radicals; and B and Y are each independently selected from aryl radicals, tertiary alkyl radicals, and tri(hydrocarbyl)silyl radicals.

17. The composition of claim 16 wherein each R$^3$, R$^4$, R$^5$, R$^6$, A and Z is independently selected from the group consisting of hydrogen, halogen alkyl, aryl, alkaryl, aralkyl, alicyclic, alkoxy, aryloxy, hydrocarbyl carbonyl [—C(O) R$^7$], hydrocarbyl carboxy [—OC(O)R$^7$] (wherein R$^7$ is a monovalent hydrocarbyl radical), and tri(hydrocarbyl)silyl radicals; the aforementioned organic, hydrocarbyl, and tri (hydrocarbyl)silyl radicals each comprising from 1 to about 20 carbon atoms.

18. The composition of claim 16 wherein each A is independently selected from hydrogen, chloro, bromo, iodo, methyl, ethyl, tertiary butyl, isoamyl, tertiary amyl, tertiary octyl, methoxy, acetyl [CH$_3$C(O)—], propionyl [CH$_3$CH$_2$C (O)—] and trimethylacetoxy [(CH$_3$)$_3$C—C(O)O—] radicals; and each Z is independently selected from tertiary butyl, tertiary amyl, tertiary octyl, tri(methyl)silyl, tri(ethyl) silyl, xylyls, dimethylphenyls, diethylphenyls, trimethylphenyls, and trimethylacetoxy radicals.

19. The composition of claim 16 wherein B and Y are each independently selected from aryl radicals, tertiary alkyl radicals, and tri(hydrocarbyl)silyl radicals having from 3 to about 30 carbon atoms.

20. The composition of claim 16 wherein each B is independently selected from tertiary butyl, trimethylsilyl, phenyl, dimethylphenyl, and trimethylphenyl radicals.

21. The composition of claim 1 being selected from the following species:

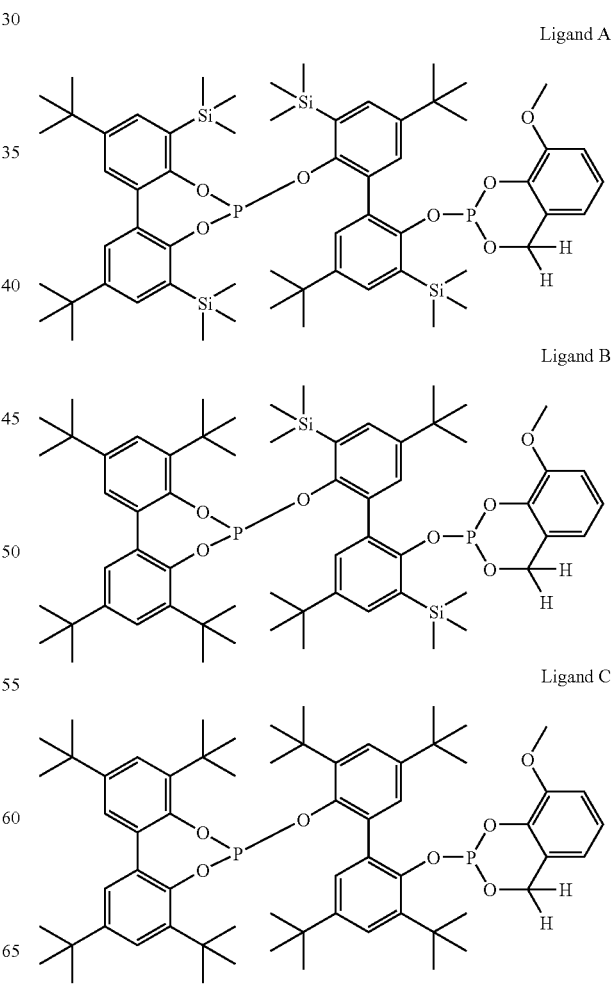

-continued

Ligand D

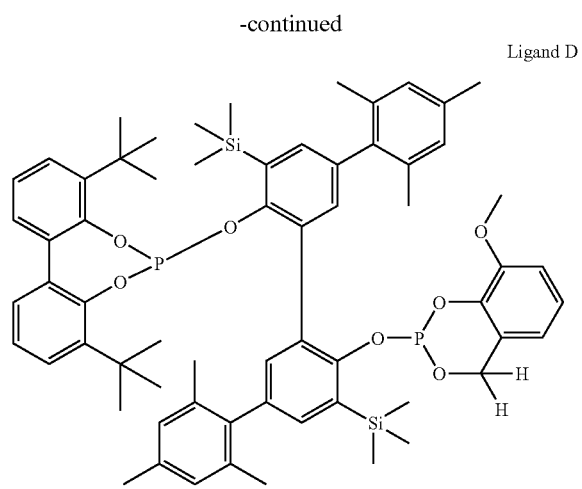

Ligand E

Ligand F

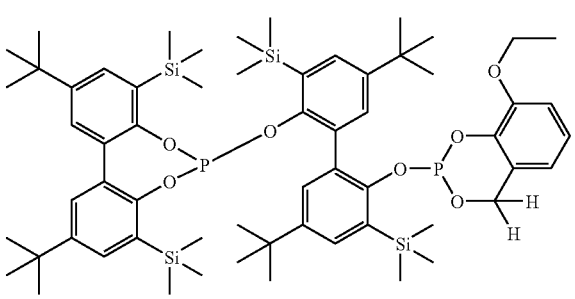

Ligand G

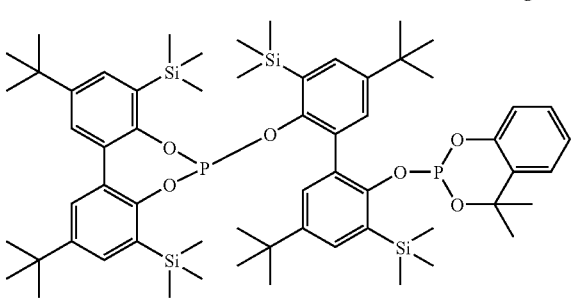

-continued

Ligand H

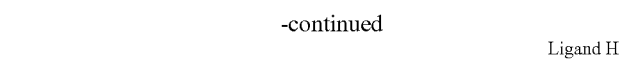
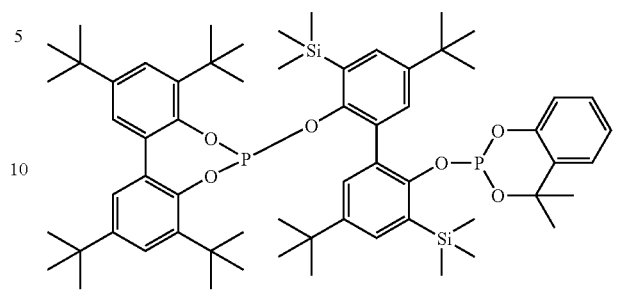

Ligand I

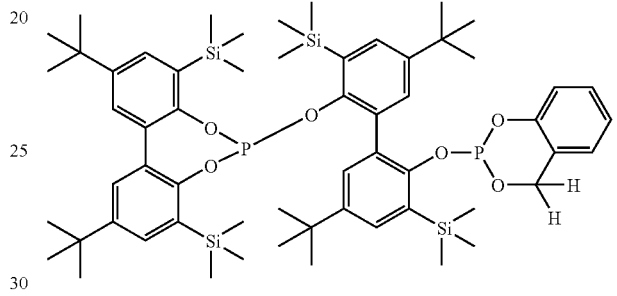

Ligand J

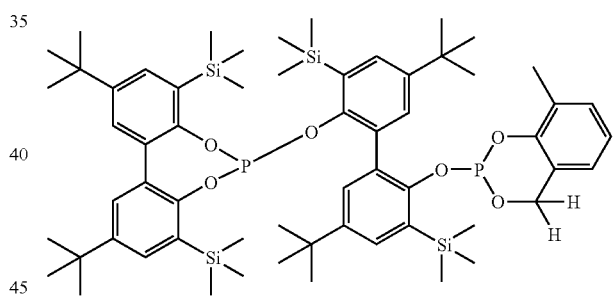

22. A transition metal complex catalyst or complex catalyst precursor comprising a Group VIII transition metal bonded to at least one molecule of ligand of claim 1, optionally, further bonded to carbon monoxide, hydrogen, or both carbon monoxide and hydrogen.

23. The composition of claim 22 wherein the Group VIII transition metal is selected from ruthenium, rhodium, cobalt, and iridium; and the ligand is selected from the compositions of claim 16.

24. A solution comprising an organic solvent, free ligand, and a transition metal complex catalyst or complex catalyst precursor composition comprising a Group VIII transition metal bonded to at least one molecule of ligand, wherein the bonded and optionally the free ligands have the formula of claim 1.

25. The solution of claim 24 wherein the Group VIII transition metal is selected from the group consisting of ruthenium, rhodium, cobalt, and iridium; and wherein the bonded and optionally the free ligands are independently selected from the group consisting of the ligands shown in claim 1.

26. A carbonylation process comprising contacting an organic compound capable of being carbonylated with carbon monoxide in the presence of a transition metal complex catalyst comprising a Group VIII transition metal bonded to at least one molecule of ligand, optionally, in the presence of free ligand; wherein the bonded and optionally the free ligands have the formula shown in claim 1, the contacting being conducted under carbonylation conditions sufficient to prepare the corresponding carbonylated organic compound.

27. The process of claim 26 wherein the carbonylation comprises a simple carbonylation, hydroformylation, hydroacylation, hydrocyanation, hydroamidation, hydroesterification, or hydrocarboxylation.

28. The process of claim 26 wherein the Group VIII transition metal is selected from ruthenium, rhodium, cobalt, and iridium; and wherein the bonded and optionally free ligands are each independently selected from the ligands listed in claim 16.

29. The process of claim 26 comprising a hydroformylation process wherein an olefinically unsaturated aliphatic hydrocarbon containing from 2 to about 60 carbon atoms and one or more unsaturated groups is contacted with carbon monoxide in the presence of hydrogen.

30. The carbonylation process of claim 29 wherein the olefinically unsaturated aliphatic hydrocarbon is selected from the group consisting of alpha olefins, internal olefins, alkyl alkenoates, alkenyl alkanoates, alkenyl alkyl ethers, and alkanols.

31. The carbonylation process of claim 29 wherein the olefinically unsaturated aliphatic hydrocarbon is selected from the group consisting of ethylene, propylene, 1-butene, 1-pentene, 1-hexene, 1-heptene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethylhexene, styrene, 3-phenyl-1-propene, butadiene, 1,3-cyclohexadiene, 1,4-cyclohexadiene, 1,7-octadiene, 3-cyclohexyl-1-butene, allyl alcohol, hex-1-en-4-ol, oct-1-ene-4-ol, vinyl acetate, allyl acetate, 3-butenyl acetate, vinyl propionate, 1-vinyl-3-cyclohexene, allyl propionate, allyl butyrate, methyl methacrylate, 3-butenyl acetate, vinyl ether, vinyl methyl ether, allyl ethyl ether, n-propyl-7-octenoate, methyl 1-decenoate, 3-butenenitrile, 5-hexenamide, methyl oleate, soybean oil and castor oil.

32. The carbonylation process of claim 26 wherein the process is conducted in the presence of a solvent selected from the group consisting of saturated hydrocarbons, aromatic hydrocarbons, ethers, aldehydes, ketones, nitriles, and aldehyde condensation products; at a molar ratio of ligand to Group VIII transition metal greater than about 1.1/1 and less than about 100/1.

33. The carbonylation process of claim 26 wherein the carbonylation is conducted at a process temperature greater than about 30° C. and less than about 200° C. and at a total pressure greater than about 1 psia (7 kPa) and less than about 10,000 psia (68,948 kPa).

34. The carbonylation process of claim 26 wherein the carbon monoxide partial pressure is greater than about 1 psia (7 kPa) and less than about 500 psia (3446 kPa); and wherein in a hydroformylation process, the hydrogen partial pressure is greater than about 5 psia (35 psia) and less than about 500 psia (3446 kPa); and wherein the $H_2/CO$ molar ratio of gaseous hydrogen to carbon monoxide is greater than about 1/10 and less than about 100/1.

35. The process of claim 1 wherein W is selected from formulas II, IV, and V.

* * * * *